April 25, 1972 B. O. WARREN Plant Pat. 3,138

BLUEGRASS PLANT

Filed Sept. 18, 1969

Inventor:
Benedict O. Warren
By: Hofgren, Wegner, Allen, Stellman & McCord
Attorneys United States Patent Office Plant Pat. 3,138
Patented Apr. 25, 1972

3,138

BLUEGRASS PLANT

Benedict O. Warren, 8400 W. 111th St.,
Palos Park, Ill. 60464

Filed Sept. 18, 1969, Ser. No. 859,215
Int. Cl. A01h *5/00*
U.S. Cl. Plt.—88 1 Claim

ABSTRACT OF THE DISCLOSURE

A Kentucky bluegrass having an extremely high turf density, the individual blades being very stiff in comparison to the well-known bluegrasses and exhibiting an upright and erect growth pattern in mowed turf. The plant in varied geographical areas has exhibited an extremely high degree of resistance to bluegrass plant diseases and has a low diploid chromosome number in comparison with other well-known bluegrasses.

The present invention relates to a new and distinct selection of a perennial bluegrass plant which was discovered by me on well-maintained and cultivated land near Chicago, Ill.

The original clone of plant material was brought by me to my nursery in Palos Park, Ill. where it was increased vegetatively in my greenhouse and outdoors to provide additional plant material for observations, tests and evaluation. The plant material of the instant invention has been observed by me for nearly 10 years in Palos Park, Ill. and it has been observed in other geographical areas throughout the country by me and qualified independent observers for more than five years.

The plant material of the original clone, after sufficient material had been vegetatively reproduced, was set out in row planting for evaluation of seed production, and it was set out in sod plots at Palos Park, Ill. and in other geographical areas for evaluation and comparison with other well-known bluegrass plants.

As a result of tests and observations of the instant bluegrass in many geographical areas of the United States, it was recognized by me that this bluegrass had certain unusual properties which gave it distinct advantages for turf use over other varieties of Kentucky bluegrass which were being commercially sold and other varieties which have been under similar tests and evaluations. The instant bluegrass has exhibited an extremely high level of disease resistivity as compared to other bluegrass varieties currently on the market, this disease resistance appearing to have a broad base and extending to powdery mildew, leaf spot, stripe and flag smut, stem rust and stripe rust and fusarium blight. As a result of this unusual disease resistance, the instant bluegrass grows vigorously and forms a very dense turf capable of suppressing the encroachment of undesirable plants. The leaf structure of the instant bluegrass turf is physically distinctive and is characterized by its upright and erect growth pattern. The individual leaves are extremely stiff in comparison to other well-known commercial bluegrasses.

A primary object of the present invention is to provide a new and distinct bluegrass plant having the characteristics described above, which characteristics will be described in greater detail hereinafter.

THE DRAWINGS

The instant bluegrass is illustrated, and certain features are pointed out, in the accompanying colored photographs, in which:

FIG. 1 is a view of a portion of an experimental sod plot, approximately the right-hand half being the instant bluegrass plant and the left-hand half being Merion bluegrass, the plot having been maintained under identical environmental and mowing conditions to illustrate the upright and erect growth pattern of the instant bluegrass as compared to the angular leaf growth pattern of Merion bluegrass;

Figure 5:
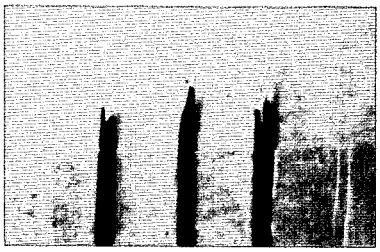
Figure 6:
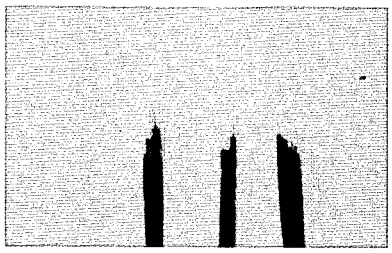

FIG. 5 is a photograph of three leaf blades of the instant bluegrass which were randomly selected immediately after mowing by a rotary mower and showing exposed vascular strands; and FIG. 6 is a photograph showing three blades of Merion bluegrass mowed at the same time and with the same mower as the blades of FIG. 5 and randomly selected immediately after mowing, the photograph illustrating vascular strands in fewer numbers and of shorter length in comparison to the instant bluegrass shown in FIG. 5.

CLASSIFICATION

The instant bluegrass plant exhibits the characteristics and properties which indicate that it belongs broadly in the Kentucky bluegrass classification (*Poa pratensis L.*). The instant bluegrass exhibits the typical flowering stalk and seed characteristic of the Kentucky bluegrass classification, but it is unique and distinct from other varieties and selections of Kentucky bluegrass when maintained as turf. It has far less susceptibility to those bluegrass diseases which commonly attack and parasitize other varieties of Kentucky bluegrass. In physical properties, the instant plant produces an extremely stiff, upright and erect leaf, and the plants develop an exceedingly dense turf which successfully resists the intrusion of other plants or weeds. In addition, the instant blant has an exceedingly low chromosome number as compared to the numbers of other well-known bluegrass plants.

GROWTH CHARACTERISTICS

The instant bluegrass is a perennial plant. The appearance of unclipped mature plants is typical of the Kentucky bluegrass classification. At inflorescence, the flowering stalk is generally 1 to 2 feet in height, and the panicle is somewhat spreading. However, the height may vary depending upon the geographical and environmental conditions, and generally the instant plant attains a substantially greater height on the U.S. Pacific Coast, for example, than it does in the Midwest.

Figure 1:
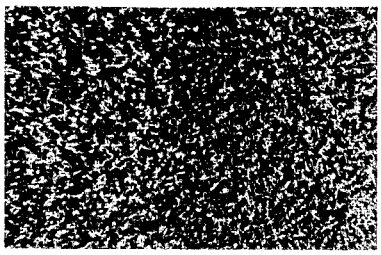

One of the principal features of the instant bluegrass is that under cultivation it attains a density of turf which is considerably greater than that of any of the commercial bluegrasses that have been under observation. This density factor, combined with is exceptional disease resistance, minimizes the problem of weed invasion. The righthand portion of FIG. 1 illustrates the extreme density of the turf which density makes it necessary to remove the clippings during or following mowing at the lower mowing heights because the clippings are not able to nest into or to disappear into the dense leaves of the turf. Even at mowing heights of 2 to 2½ inches, the leaf blades remain very stiff and stand erectly. This erectness is far greater than the bluegrass of Plant Patent No. 2,887 (Fylking bluegrass) or a selection known as Pennstar bluegrass, and it is considerably greater than Merion bluegrass, for example, note the Merion turf at the left in FIG. 1. The instant bluegrass retains its good density quality even under short mowing as will be subsequently discussed.

A study and evaluation of certain growth characteristics of the instant bluegrass was made in comparison to a number of well-known commercial bluegrasses. As to each of the bluegrass plants which were compared, many sod plugs of identical size were taken from adjacent turf plots that had been well maintained under substantially identical environmental and geographical conditions. An average calculation or count was made of live shoots per square inch and of live leaves per square inch. The removal of the sod plugs and the completion of the count was accomplished in four days in the month of July. All of the turf plots used in the evaluation were four years old and had been well-maintained at a 1½ inch mowing height for at least two years.

The average count of live shoots per square inch revealed:

Plant Patent No. 2,887 (Fylking bluegrass)—17.99 live shoots per square inch.
Plant Patent No. 2,364 (Windsor bluegrass)—17.61 live shoots per square inch.
Plant Patent No. 2,615—20.47 live shoots per square inch.
Merion bluegrass—22.84 live shoots per square inch.
The instant bluegrass—26.61 live shoots per square inch.

In the same manner as pointed out above, the average number of live leaves per square inch was calculated comparing the instant bluegrass with those bluegrasses set out above. This count revealed:

Plant Patent No. 2,887 (Fylking bluegrass)—56.25 live leaves per square inch.
Plant Patent No. 2,364 (Windsor bluegrass)—51.76 live leaves per square inch.
Plant Patent No. 2,615—56.76 live leaves per square inch.
Merion bluegrass—70.32 live leaves per square inch.
The instant bluegrass—77.81 live leaves per square inch.

In order to ascertain density retention qualities under short mowing, the instant bluegrass was compared with Merion bluegrass and Fylking bluegrass, each of the plots having been maintained for over 4 years at a 7/16 inch mowing height under substantially identical environmental conditions. The counts were carried out in the same manner as indicated above and revealed:

Plant Patent No. 2,887 (Fylking bluegrass)—25 live shoots per square inch.
Merion bluegrass—56.47 live shoots per square inch.
The instant bluegrass—41.55 live shoots per square inch.

As to live leaves per square inch, the count revealed:

Plant Patent No. 2,887 (Fylking bluegrass)—119.01 live leaves per square inch.
Merion bluegrass—165.49 live leaves per square inch.
The instant bluegrass—166.76 live leaves per square inch.

A comparison was also made of the average number of inches of rhizomes per square inch of sod produced by the instant bluegrass as compared with a number of other well-known bluegrasses. Six identical sod plugs were taken at random from turf plots of each of the bluegrasses. The removal of the sod plugs and the completion of the measurements was accomplished over the period of about three successive days in the month of July. Each of the turf plots was four years old and well-maintained at a 1½ inch mowing height for at least two years under substantially identical environmental conditions. This comparison revealed the following average count:

Plant Patent No. 2,887 (Fylking bluegrass)—27 lineal inches of rhizomes per square inch.
Plant Patent No. 2,364 (Windsor bluegrass)—5 lineal inches of rhizomes per square inch.
Plant Patent No. 2,615—11 lineal inches of rhizomes per quare inch.
Merion bluegrass—5 lineal inches of rhizomes per square inch.
The instant bluegrass—13 lineal inches of rhizomes per square inch.

Thus it is seen that the instant bluegrass is a good producer of live shoots and live leaves whether the turf is maintained at average height or extremely short. While one of the observed bluegrasses was a greater rhizome producer, the instant bluegrass rated second and was an impressive rhizome producer.

LEAF CHARACTERISTICS

Measurements of leaf width were made at my nursery in Palos Park, Ill. from well-maintained four year old turf plots which had been regulary mowed to a 1½ inch height for at least two years. The second leaf of each tiller was selected for measurement at the widest part of each such leaf. The average leaf width was calculated by taking an average of hundreds of measured leaves.

The average leaf width of the instant bluegrass was found to be 1.9 mm., which was slightly less than the average of Windsor bluegrass (Plant Pat. No. 2,364) and Fylking bluegrass (Plant Pat. No. 2,887), although many leaves of Fylking were less than the 1.9 mm. average of the instant bluegrass. Merion bluegrass leaves were very nearly the same average width as the instant bluegrass, while the bluegrass of Plant Pat. No. 2,615 was narrower by about .3 mm.

Thus, the average leaf width of the instant bluegrass approximates the leaf width of Merion bluegrass. In FIG. 1, which is a viewlooking directly downwardly at the turf the instant bluegrass is shown at the right and Merion bluegrass turf is shown at the left. Both turfs shown in FIG. 1 had been recently mowed under identical conditions in the same direction and with the mower set approximately 1½ inch in height. Many of the leaves of the Merion turf are shown inclined to the vertical, because they do not have the stiffness to stand erectly and to grow uprightly as is the case of the instant bluegrass turf on the right. However, the leaf width on an average is approximately the same in each of the turf plots, the difference in visual appearance being caused by the unique physical characteristic of the growth pattern of the instant bluegrass leaves.

Another characteristic of the instant bluegrass relates to the color of its leaves during the growing season. Under similar conditions of environment and propagation, the leaf color of the instant bluegrass plant is a considerably darker green than that of the Merion bluegrass plant in the spring months and in the fall months. However, during the summer months, the leaves of the instant bluegrass plant assume a slightly lighter shade of green than the color of the leaves of the Merion bluegrass plant. The above observations relating to leaf color have been made over a number of years at my nursery in Palos Park, Ill.

FIG. 5 illustrates three randomly selected leaves of the instant bluegrass plant, while FIG. 6 illustrates three randomly selected leaves from Merion bluegrass turf. The turf plots from which the leaves of FIGS. 5 and 6 where taken were recently mowed by the same mower, moving in the same direction and operating at the same height. A rotary mower was used to perform the cutting. The turf plots were each several years old and each was well-maintained under identical environmental conditions.

One of the unique features of the instant bluegrass is the relative toughness, stiffness and strength of the leaves as compared to other bluegrass plants. For example, the leaves in turf of the instant bluegrass are sufficiently dense, erect and stiff such that the leaves readily support the weight of a golf ball in a position much higher than is the case with other bluegrass plants. This stiffness, and toughness is believed to be related to the vascular bundles in each leaf of the instant bluegrass. For example, in FIG. 5, the tufts of the vascular strands can be seen extending upwardly, and these strands are considerably longer and more vascular strands are present than in the Merion bluegrass in FIG. 6. In other words, the vascular strands of the leaves of the instant bluegrass resisted the rotary mower cutting action to a greater degree. FIG. 5 illustrates typically the appearance after rotary mower cutting action. Thus, it takes a finely adjusted reel type mower to precisely cut or shear the instant bluegrass so as not to leave the frayed tips and vascular strands as shown in FIG. 5 which tips subsequently "brown out" sometime after mowing.

CYTOLOGICAL CHARACTERISTICS

One of the principal distinguishing characteristics of the instant bluegrass plant is its extremely low diploid chromosome number, which number is considerably lower than any known to me as a result of my investigations and my reading of the published literature relating to the well-known commercial bluegrass plants. From laboratory investigations and observations, the chromosome number of the instant novel bluegrass plant is approximately 2n is equal to 38.

In marked contrast, published literature indicates that the chromosome number for Delta bluegrass is about 71 and for Newport bluegrass is about 81. In addition, the chromosome number of the bluegrass plant shown and described in U.S. Plant Patent 2,364 is about 86; in my U.S. Plant Patent 2,615 it is about 48; while U.S. Plant Patent 2,887 lists a number of approximately 72–76, and states that numbers have been observed as high as 122.

REPRODUCTION

The instant bluegrass does not appear to be completely apomictic. Seeds from the parent plant have not uniformly produced other parent plants. The planting of seeds of the parent plant has yielded approximately 80% apomictically formed plants and approximately 20% sexually developed plants.

Thus, reproduction of the novel instant bluegrass plant has been carried out by vegetative propagation. The parent plant of the instant bluegrass has been asexually reproduced many, many times by utilizing rhizomes created by the parent plant; and subsequent propagation of the instant bluegrass from rhizomes have always resulted in additional identical parent plants. In other words, no sporting has been observed at any time.

Thus, the asexual reproduction of the instant bluegrass plant by utilizing rhizomes for vegetative propagation of uniform bluegrass plants have been found to be genetically the same as the parent plant in growth characteristics and behavior through many successive generations of propagation.

DISEASE RESISTANCE

The most unique feature of the instant bluegrass plant has been its extremely high level of disease resistance to those common and ordinary disease to which well-known commercial types of Kentucky bluegrasses have been found to be susceptible. This disease resistance has been observed in many geographical locations from coast to coast throughout the United States. Observations of this resistance have been made by independent and competent observers over a period of years in New Jersey, Ohio, Illinois, Indiana, Missouri, Wisconsin and in Calif. The observations have been made and compared with other well-known Kentucky bluegrasses grown under similar environmental conditions as the instant bluegrass plant.

(1) Powdery mildew

It has been commonly reported that the bluegrass plant disease referred to as "powdery mildew" is caused by the fungus *Erysiphe graminis*. Observations of the instant bluegrass plant have been made in the geographical areas referred to above, and these observations indicate that the instant plant has almost complete immunity to powdery mildew. While there are many strains of the fungus causing this disease, the observations have demonstrated in all locales an extremely high level of resistance, and thus great resistance to the many strains of this disease-causing fungus.

Figure 2:
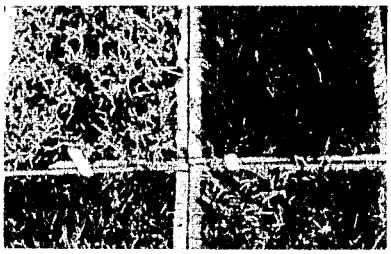
FIG. 2 is a view of two adjacent sod selections, the upper right-hand selection being the instant bluegrass and the upper left-hand selection being Merion bluegrass, the figure illustrating the resistance of the instant bluegrass to powdery mildew as compared to the susceptibility of Merion bluegrass to this disease.

FIG. 2 of the drawings shows the instant bluegrass plant at the upper right as compared with Merion bluegrass on the upper left, with both bluegrass plants having been maintained under similar environmental conditions. It will be noted that the Merion bluegrass plants have been severely attacked by powdery mildew, while the instant bluegrass plant flourished and was unaffected by the disease.

Figure 3:
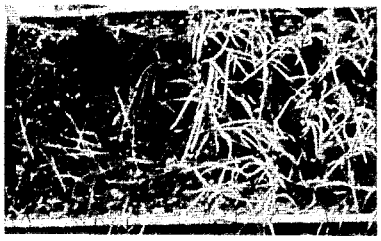
FIG. 3 is a view showing a number of spaced plants of two adjacent sod selections, the bluegrass plants on the right being Merion bluegrass and those on the left being the instant gluegrass, the figure again illustrating the resistance of the instant bluegrass to powdery mildew as compared to the susceptibility of Merion bluegrass.

Similarly in FIG. 3, tillers of the instant bluegrass plant are arranged on the left while tillers of Merion bluegrass are on the right. Again, under similar environmental conditions the Merion bluegrass tillers have been severely attacked by powdery mildew, while the instant bluegrass tillers have remained unaffected.

(2) Leaf spot

The disease commonly called leaf spot is reportedly caused by ony one of several Helminthosporium species. In the opinion of some well-recognized pathologists, certain of the species has an increased prevalence depending upon the particular geographical area. Thus, in Minnesota the most frequently isolated pathogen of this genus is *Helminthosporium* dictyoides; in Illinois, *Helminthosporium sativum* (*Helminthosporium sorokinianum*) is reported most frequently; while in the eastern part of the United States *Helminthosporium* vagans is generally considered to be the most prevalent pathogen. The instant bluegrass plant has indicated a superior resistance to leaf spot generally, and to the above Helminthosporium species, in particular, in observations made in New Jersey, Ohio, Indiana, Illinois, Wisconsin, Missouri and California.

On occasion during the cooler months in certain scattered individual tillers of the instant bluegrass plant, very sparce leaf spotting has occasionally been noticed. From the lesions on these tillers, a species of Helminthosporium has been isolated, but the species has not as yet been identified. However, the general over-all resistance to the disease leaf spot has continued to be superior in the instant bluegrass plant in comparison to other well-known bluegrasses throughout the varied geographical areas of observation.

(3) Stripe and flag smut

The disease generally known as stripe smut is caused by the pathogen *Ustilago striiformis;* and the disease commonly known as flag smut is reported to be caused by the pathogen *Ustilago agropyii*. The instant bluegrass plant, from observations in New Jersey, Ohio and Illinois, appears to have excellent resistance to both of the above pathogens as compared to other well-known bluegrasses. These are characteristic symptoms of the above smut organisms which have been found in other commercial bluegrasses in the above locales, and each of the smut organisms has been isolated from the infected bluegrasses. However, in adjacent sod plots in the same locales over a period of five years, the instant bluegrass plots have been inspected and none of the symptoms of stripe and flag smut have shown up.

Figure 4:
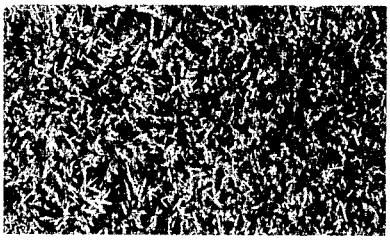
FIG. 4 is a view of two adjacent sod selections maintained under similar environmental and mowing conditions and illustrating the resistance of the instant bluegrass to smut, the instant bluegrass being on the right and Merion bluegrass being on the left, and the smut disease having substantially decreased the density of the Merion bluegrass.

In FIG. 4, the instant bluegrass plant is shown on the the right while Merion bluegrass plants are shown on the left. Again, both sections of turf were maintained under similar environmental conditions. Stripe and flag smut was observed to have seriously attacked the Merion bluegrass plants such as to reduce seriously the density of the turf, while the instant bluegrass plants showed excellent resistance to both of these pathogens and maintained its turf density in a superior fashion.

(4) Stem and rust and stripe rust

The disease commonly referred to as stem rust is reportedly caused by the fungus *Puccinia graminis,* which fungus has many physiological strains. Observations over a number of years have indicated that the instant bluegrass plant is highly resistant to many of the strains of the above fungus; however, in some observations in Illinois, this pathogen has been found in modest amounts on the instant bluegrass plant. Thus, it appears that the instant plant is high resistant to many strains of the fungus and has moderate to high resistance to other strains.

Stripe rust, reportedly caused by the fungus *Puccinia striiformis,* has only been observed by me near Suisun City, Calif. in test plots of the instant bluegrass plant. The results of these observations have been limited to only two years. The instant bluegrass plant has shown moderate susceptability to stripe rust, but it has shown better resistance than most of the well-known commercial bluegrass plants and at least as good resistance as certain others, for example, Newport and Windsor bluegrass plants. Stripe rust is apparently indigenous to California, although its presence has been noted in wheat (as well as bluegrass) from about San Francisco, Calif. north to the state of Washington.

(5) Fusarium blight

Fusarium blight is reportedly caused by *Fusarium roseum* and/or *Fusarium tricinctum.* Observations in respect to this disease have been carried out with regular frequency over a period of years in test plots in St. Louis, Mo. The plots include 16 experimental selections and, in addition, plots of Delta, Newport, Merion and common Kentucky bluegrasses. While the instant bluegrass plant is modestly susceptible to Fusarium blight, seven years of observation have indicated that the instant bluegrass plant is rated as second in resistance to this pathogen as compared to the bluegrasses of the other 19 plots. Thus, its resistance is also considerably above average to this disease.

In my disease resistance observations, in and around my nursery in Palos Park, Ill., I have observed the instant bluegrass plant as compared to nearly 350 other bluegrass plant selections which have been regularly observed in well-maintanied plots under substantially identical environmental conditions. The instant bluegrass plant exhibits by far the best and broadest range of disease resistance of any of the bluegrasses observed at Palos Park, Ill. Independent observers in Ohio and in New Jersey have reported similar results in respect to the instant bluegrass plant after observations of several years. Thus, perhaps the most important single feature of the instant bluegrass plant is its superior over-all resistance to those diseases to which the usual varieties of bluegrass plants are susceptible.

What I claim and desire to be secured by Letters Patent is:

1. The new and distinct variety of bluegrass plant, substantially as shown and described herein, characterized particularly by a very high resistance to common diseases of bluegrass plants and a capability of forming an exceedingly tight and dense turf with the leaves being unusually stiff, erect and resistant to shearing forces, said variety having a relatively low diploid chromosome number as compared to other known varieties of bluegrass plants.

No references cited.

ROBERT E. BAGWILL, Primary Examiner